United States Patent [19]

Sakurai

[11] 3,932,670
[45] Jan. 13, 1976

[54] METHOD OF MANUFACTURING A BACTERIAL PREPARATION CONSISTING OF A NORMAL RUMEN BACTERIAL FLORA WITH AN IMPROVED ABILITY TO UTILIZE AMMONIUM SALTS

[75] Inventor: Nobuo Sakurai, Chiba, Japan

[73] Assignee: Miyairi Kinzai Kenkyusho Company Limited, Japan

[22] Filed: May 24, 1973

[21] Appl. No.: 363,558

[30] Foreign Application Priority Data
May 29, 1972 Japan............................. 47-53122

[52] U.S. Cl. ..................... 426/2; 195/79; 195/76; 195/112
[51] Int. Cl.² ....................... C12K 1/00; C12K 3/00
[58] Field of Search .............. 426/2, 42, 43, 52, 53, 426/61, 69, 71, 807; 195/76–79, 96, 112

[56] References Cited
UNITED STATES PATENTS
2,700,611  1/1965   Jeffreys................................ 426/71
3,243,299  3/1966   Mecho.................................. 426/61
3,857,971  12/1974  Abdo et al............................ 426/53

Primary Examiner—Lionel M. Shaprio
Attorney, Agent, or Firm—James C. Haight

[57] ABSTRACT

A method of manufacturing a bacterial preparation for ruminants which comprises taking out ruminant-stomach bacterial groups from the rumen of a ruminant grown under an excellent condition, repeatedly inoculating by the streak method and culturing the bacterial groups on a same selective medium containing an ammonium salt, gradually increasing the medium while serially passing the bacteria on the medium, allowing certain microorganisms of the bacterial groups to utilize the metabolic products of the bacteria, thereby obtaining bacteria having an improved ammonium-utilizing ability, and then using the improved bacteria as a principal ingredient of a bacterial preparation.

8 Claims, 3 Drawing Figures

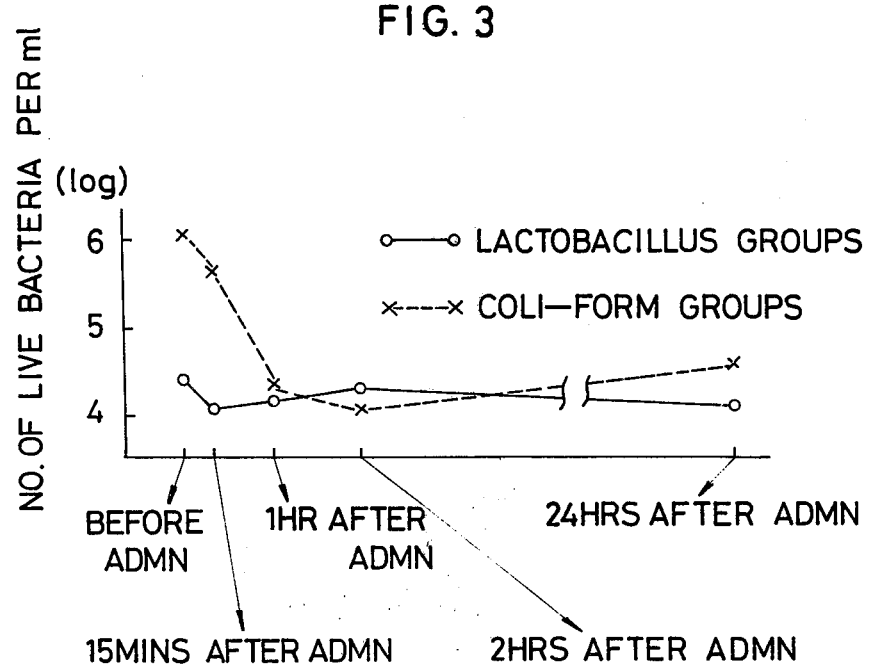

METHOD OF MANUFACTURING A BACTERIAL PREPARATION CONSISTING OF A NORMAL RUMEN BACTERIAL FLORA WITH AN IMPROVED ABILITY TO UTILIZE AMMONIUM SALTS

This invention relates to a method of manufacturing a bacterial preparation of a normal rumen bacterial flora with an improved ability to utilize ammonium salts.

The digestive system of ruminating animals is characterized by a stomach of four chambers, namely, the rumen, reticulum, omasum, and abomasum, of which the first-mentioned chamber plays a vital role for the digestion of foods. Carbohydrates in the feeds for the ruminants are converted by the bacterial action in the rumen into sugars and thence into lower fatty acids such as butyric acid, acetic acid, and lactic acid. Also, proteins in the feeds are decomposed by the enzymes secreted by the microbes in the rumen into peptides, amino acids and the like, which in turn give birth to ammonia and lower fatty acids. Of those digestion products, ammonia is effectively utilized by the rumenal microbes in the resynthesis of bacterial somatic proteins, which are subsequently absorbed by the animals as an energy source therefor. Thus, in the case of ruminants, it is a problem of important significance to maintain the equilibrium of the bacterial floras in their rumens and efficiently transfer the ammonia into the bacterial somatic proteins.

Now if a feed having high protein contents or a urea feed is given to excess, more than this necessary ammonia will be produced for the digestive organs of some ruminants. The excess ammonia will increase the percentage of blood ammonia until it poisons the animals. In addition, the equilibrium of the rumenal flora will be lost, for example, with decreases in the numbers of live lactic acid bacteria and colon bacteria, and thus the ammonia poisoning will be further promoted.

The present invention has for its object to prevent the ammonia poisoning and loss of the equilibrium of the rumenal flora in the ruminants due to overfeeding with high-protein or urea-based food, by taking out groups of bacteria from the rumens of ruminants grown under an excellent condition, improving the ammonia-utilizing ability of the bacteria, and then feeding the improved microorganisms together with the high-protein or urea-based rations to the mammals.

The expression "excellent condition" as used herein in connection with the growing of ruminants means feeding a mixed food of an excellent composition to the animals, as contrasted with "inferior condition" under which the animals are caused to take a poor diet. Generally, an abundant supply of cellulosic foods, such as green forages, is believed desirable because it stimulates the rumination. Then, it may be said that a diet containing a large proportion of roughage or green grass for example is an excellent condition, whereas a feed with less cellulosic or grassy contents is an inferior condition. The excellent and inferior feed compositions are exemplified in the following table.

| Compositions of mixed feeds (per head per day) | | |
|---|---|---|
| Feed ingredient | Inferior condition | Excellent condition |
| Concentrated mixture | 0.5 kg | 9.0 kg |
| Wheat bran | 0.7 | — |
| Imported wheat | 0.9 | — |
| Hay cubes | 1.5 | — |
| Beet pulp | 1.5 | 1.0 |
| Strained lees of bean-curds | 10.0 | — |
| Brewer's grains | 10.0 | — |
| Straw | 1.0 | 3.0 |
| Special bran | — | 3.0 |
| Silage | — | 15.0 |
| Green forage | — | 5.0 |

Feeding under such an excellent condition promotes the rumination and facilitates the fermentation in the rumen. On the other hand, the feed of such an inferior formula makes the rumination relatively slow, interrupts smooth fermentation in the rumen, and builds up harmful decomposition products in the stomach, which when internally absorbed by the animal will cause putrefaction of the rumen, hoven, scours, and also wind colic with excessive internal ammonia accummulation.

FIG. 3 is a similar graph showing changes with subacute administration of urea.

Figure 1:
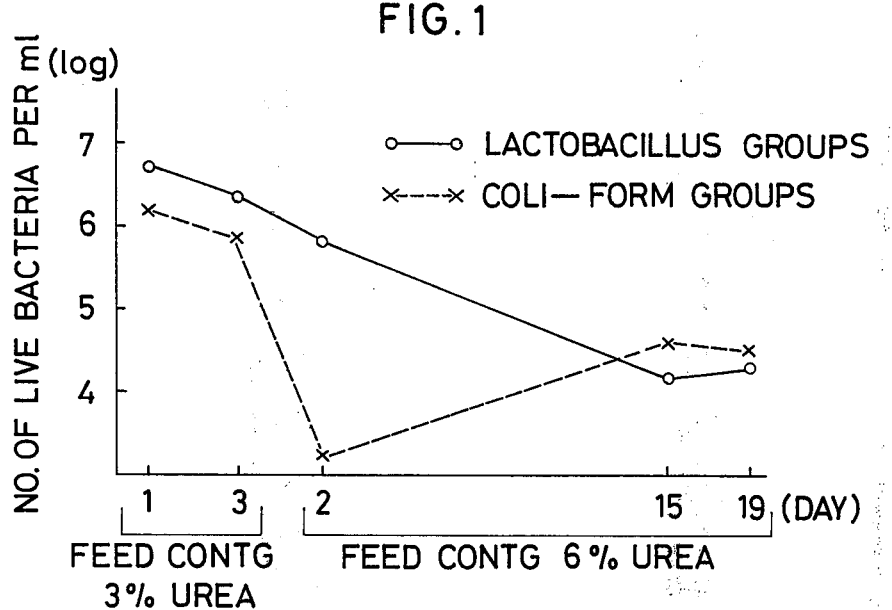
FIG. 1 is a graph showing changes in the viable counts of the bacterial floras in the rumens of goats with feeding on foods containing different proportions of urea.

In search of bacterial groups adapted to be improved in their ammonia-utilizing abilities, we conducted the following experiments.

Test cows were raised under excellent and inferior conditions, and their rumenal juices were examined in the usual manner for viable counting of the lactobacillus and coli-form groups present therein.

The results are compiled in Table 1. Usually the greater the number of lactobacillus groups, the smaller the number of coli-form groups. As shown, the results indicated that the bacterial floras in the rumens of the cows fed under an inferior condition contained more lactobacillus and coli-form groups than in those of the cattle grown under an excellent condition. This demonstrates the fact that the lactobacillus groups in the rumens of the cows fed under an inferior condition include large proportions of lactobacillus groups which have only weak inhibiting actions upon the multiplication of coli-form groups as compared with those in the cows grown under an excellent condition.

Table 1

| Bacteria in the rumens of cows fed under an excellent condition | | |
|---|---|---|
| Milking cow | Lactobacillus group | Coli-form group |
| $N_1$ - 1 | $1.1 \times 10^6$ | $2.8 \times 10^4$ |
| " - 2 | $2.0 \times 10^6$ | $7.0 \times 10^5$ |
| $N_2$ - 1 | $2.0 \times 10^5$ | $7.0 \times 10^3$ |
| " - 2 | $2.0 \times 10^6$ | $4.0 \times 10^5$ |
| $N_3$ - 1 | $2.0 \times 10^6$ | $1.0 \times 10^5$ |
| " - 2 | $1.2 \times 10^6$ | $1.0 \times 10^5$ |

| Bacteria in the rumens of cows fed under an inferior condition | | |
|---|---|---|
| Milking cow | Lactobacillus group | Coli-form group |
| $K_1$ - 1 | $2.0 \times 10^7$ | $1.0 \times 10^6$ |
| " - 2 | $4.2 \times 10^6$ | $4.0 \times 10^6$ |
| $K_2$ - 1 | $7.5 \times 10^6$ | $2.0 \times 10^6$ |

Table 1-continued

Bacteria in the rumens of cows fed under an excellent condition

| Milking cow | Lactobacillus group | Coli-form group |
|---|---|---|
| " -2 | $1.0 \times 10^7$ | $6.0 \times 10^6$ |
| $K_3$-1 | $2.0 \times 10^7$ | $1.0 \times 10^6$ |
| " -2 | $2.0 \times 10^7$ | $2.0 \times 10^6$ |

Note:
The numerical values given represents the viable counts or the numbers of live bacteria per milliliter of rumenal juice.

Generally speaking, it is desirable that there are a large number of lactobacillus groups and a small number of coli-form groups in the rumen. The experimental results tabulated above indicate that the bacterial floras in the rumens of the cows fed under an excellent condition are superior in bacterial activities than those of the cows grown under an inferior condition.

In view of this, the lactobacillus groups in the floras examined were identified and the results were obtained as given in Table 2.

In brief, *Lactobacillus acidophilus, Lactobacillus plantarum, Streptococcus lactis,* and *Streptococcus faecalis* were dominant in the floras of the animals fed under an excellent condition, whereas *Lactobacillus fermenti* and *Lactobacillus brevis* dominated under an inferior condition.

*Lactobacillus acidophilus, Streptococcus lactis,* and *Lactobacillus brevis* are conventional bacteria.

As already noted, it is common with ruminating animals that the proteins in the feeds are converted by the action of microorganisms in their rumens into peptides and amino acids and thence into ammonia, which in turn is resynthesized by microbic action to form bacterial somatic proteins to be utilized in vivo. Therefore, how efficiently the ammonia is resynthesized to the proteins and how its utility in this respect can be enhanced is deemed a problem of major importance in the art.

According to the present invention, a bacterial group having ammonia-utilizing ability is selected as a minority group among the lactobacillus, clostridium, cellulose-decomposing, and subtilis groups, yeast, etc. which constitute the normal rumen bacterial floras of the ruminant animals being fed under excellent conditions, the ammonia-utilizing ability of the group is improved, and the resulting group endowed with a great ammonia-utilizing ability is given to the ruminants so that the ammonia in their rumens can be efficiently transferred into the bacterial somatic proteins.

The ammonia-utilizing ability of the selected bacteria can be improved in the following way.

EXAMPLE 1

Selective culture media containing a large proportion

TABLE 2

| | Separated lactobacillus groups as identified | | | | | |
|---|---|---|---|---|---|---|
| | L. acidophilus | L. plantarum | Sc. faecalis | Sc. lactis | L. fermenti | L. brevis |
| Excellent condition | 56 | 33 | 31 | 36 | 28 | 14 |
| Inferior condition | 12 | 0 | 14 | 20 | 76 | 80 |

Note:
Each section indicates the results of identification tests conducted with 250 strains.

The tests thus suggested that *L. acidophilus, L. plantarum, Sc. faecalis,* and *Sc. lactis* are desirable lactobacillus groups for use in the present invention.

It has also been found that, when goats are amply supplied with urea-containing feed so that the ammonia concentrations in their rumens are increased, both the lactobacillus and coli-form groups tend to decrease in number, although the coli-form groups decrease once and then increase later. (FIG. 1) When placed under an adverse condition, the coli-form bacteria are multiplied free from the action of the lactic acid bacteria.

In accordance with the present invention, the bacteria with the following official strain numbers (as registered by the Japan Microbiological Industrial Technical Research Institute) may be employed:

| | |
|---|---|
| Lactobacillus plantarum | No. 1466 |
| Clostridium butyricum Miyairi | No. 1467 |
| Lactobacillus fermenti | No. 1468 |
| Streptococcus faecalis | No. 1469 | of ammonium salts, such as ammonium acetate or ammonium chloride, were used. Specifically, ammonium salt-containing, LBS-improved medium (for lactobacillus groups), sugar-ammonium-salt-containing bouillon medium (for clostridium and subtilis groups and yeast), etc. were inoculated with test strains, and the bacteria were cultured by the conventional successive transfer technique.

An instance of plate culutre carried out by that technique will now be explained. A test medium (LBS-improved medium) was streaked with 0.05 ml of a suspension of a newly cultured test strain of lactic acid bacteria (L. plantarum, U-48). From then on, in the usual manner, the test strain was then serially passed on culture media with gradually increased ammonium-salt concentrations. The results were as given in Table 4. The strain was anaerobically cultured at 37°C for 5 days. (In the table the downwardly directed arrow marks indicate that colonies on plate media were transplanted onto new media by streaking and were cultured thereon.)

TABLE 4

| Amount of ammonium salt added | Successive transfer culture of lactic acid bacteria on ammonium salt-containing media | | | | | | |
|---|---|---|---|---|---|---|---|
| | Not added | 2.5% | 5.0% | 6.0% | 7.5% | 8.0% | 8.5% |
| 1st culture | $2.4 \times 10^3$ | $2.5 \times 10^3$ | $4 \times 10$ | — | — | — | — |
| 2nd " | | | Grew all over | Grew all over | | | |
| 3rd " | | | | Grew all over | Grew all over | — | — |
| 4th " | | | | | Grew all over | — | — |
| 5th " | | | | | " | — | — |

Note:
The numerical values represent the counts of colonies on the culture media. For example, "4×10" is the number of colonies that survived on a medium containing 5.0% ammonium salt. The mark "—" indicates no growth.

As will be seen from Table 4, the serial passage of the test lactic acid bacteria on the culture media containing 8% on more ammonium salt could not yield any strain that would grow on those media.

In order to obtain a strain having a greater ammonium salt-utilizing ability, we conducted further experiments as follows. With the view to utilizing the metabolic products of the bacteria in the media, the colonies grown on the medium containing 7.5 percent ammonium salt according to the experiments given in Table 4 were spread by the streak method over the entire surface of the same plate medium. Upon the development of new colonies, they were again spread over the surface. With repetition of this procedure, each time the entire surface was covered with the colonies, the bacteria were transplanted onto a new medium. Thus, culture media having gradually increased ammonium salt concentrations were employed. It has now been found that in this way strains capable of growing on a culture medium containing as much as 10 percent ammonium salt can be obtained.

It is exemplified by the following experiment:

Thereafter, the procedure described was repeated until an ammonium salt concentration of as high as 10 percent was obtained.

As shown in Table 4, it has been impossible with conventional successive transfer culture to obtain a strain endowed with a high ammonium salt-utilizing ability when the bacteria are transplanted on culture media having 7.5 percent or more ammonium salt concentrations, despite serial passage on the media. In accordance with the present invention, by contrast, a strain whose ammonium salt-utilizing ability has been improved by the usual method is allowed to develop its colonies on a culture medium containing 7.5 percent ammonium salt (the maximum ammonium salt concentration in the conventional successive transfer culture), and the resulting medium is reused as it is, so that a strain having a greater ammonium salt-utilizing ability can be obtained.

The method of the invention is directed to the promotion of the bacterial growth not by taking advantage of the decrease in the ammonium salt concentration of the medium due to the preceding steps of culture but by permitting the bacteria to utilize the metabolic products of the bacteria already produced in the media and

| Culture medium composition and culturing procedure | | Number of colonies formed on medium |
|---|---|---|
| Medium A: | 7.5% ammonium salt added. The colony suspension of the 7.5% ammonium salt-containing medium obtained by the experiment of Table 4 was inoculated by the streak method and cultured | $3.6 \times 10^2$ |
| Medium A': | Medium A was directly used. The colonies from the medium A were spread and streaked over the entire surface of this medium, and cultured. After repetition of this, colonies developed all over the surface. | Grew all over the surface. |
| Medium B: | 8.0% ammonium salt added. A suspension of the colonies from the plate medium A' was streaked and cultured. | 7 |
| Medium B': | Medium B was directly used. The colonies from the plate medium B were spread over the entire surface of the medium, streaked and cultured. This was repeated. | $2.4 \times 10^2$ | by enabling the microorganisms to acquire the characteristic ability of utilizing high ammonium salt concentration. In this respect the method of the invention is totally different from the conventional ones.

Comparative test

A strain (A) improved in its ammonium salt-utilizing ability by successive transfer culture in the usual manner and a strain (B) improved pursuant to this invention were separately suspended in a sterilized physiological salt solution. The suspensions were streaked in amounts of 0.05 ml on the following plate culture media, and the numbers of colonies produced on culture were counted.

| Culture medium | Lactobacillus culture medium containing 9.5% ammonium salt | Lactobacillus culture medium containing no ammonium salt |
|---|---|---|
| Test strains: | | |
| Strain A (improved by usual method) | No growth | $3.5 \times 10^8$ |
| Strain B (improved by method of invention) | $5.4 \times 10^7$ | $4.1 \times 10^8$ |

Note:
The numerical values are the numbers of live bacteria per milliliter of the test suspensions.

The present method of improving the bacterial ability of utilizing ammonium salt is to enable bacteria to make most of the metabolic products of bacteria in the media. It is possible with the method to obtain a strain capable of utilizing ammonium salt in concentrations by far greater than have been possible with the strains conventionally obtained by simple successive transfer culture.

The improved strain obtained in accordance with the present invention is separated and collected, pulverized or granulated with such excipients as starches and calcium, and packaged airtight as a final preparation.

Typical compositions of one-hundred-gram preparations according to the present invention are given below:

Composition 1

| L. plantarum | 0.1 g |
|---|---|
| Cl. butyricum Miyairi | 0.1 |
| Sc. faecalis | 0.1 |
| Potato starch | 70.0 |
| Corn starch | 10.0 |
| Calcium carbonate | 19.7 |

Composition 2

| L. plantarum | 0.1 g |
|---|---|

-continued

| Cl. butyricum Miyairi | 0.1 |
|---|---|
| Sc. faecalis | 0.1 |
| L. fermenti | 0.1 |
| Potato starch | 70.0 |
| Corn starch | 10.0 |
| Calcium carbonate | 19.6 |

EXAMPLE 2

Goats were fed on a test strain of lactic acid bacteria (L. plantarum, U-48) at a rate of $4.5 \times 10^7$/kg/day and a mixed feed containing 3% ammonium salt or urea at a rate of 20 g/kg/day for one week, and then the concentration of ammonium salt or urea was gradually increased to 5, 7 and 9% in the following one-week periods. After the total prefeeding period of four weeks, the rumenal juices or excrements of the animals were inoculated and cultured on the selective media of Example 1, and the ammonium salt-utilizing abilities of the bacterial groups were determined. Most of the bacteria groups underwent mass mutation after the inoculation, and only those which exhibited good ammonium salt-utilizing abilities could be obtained.

Of the test results, those lactic acid bacteria and cellulose-decomposing bacterial will be specifically explained below.

Either ammonium sulfate (1 g/10 ml of medium) or ammonium chloride (1 g/10 ml of medium) was added to sugar-containing bouillon, and the liquid media thus prepared were inoculated with the test bacteria. The lactic acid bacteria were cultured for 48 hours, and the cellulose-decomposing bacteria for 96 hours. Thereafter the amounts of the ammonium salts consumed in the media were determined.

As is clear from Table 5, the strain of the lactobacillus group that consumed more than 0.5 g ammonium sulfate was only one out of 62 strains examined. During and after the supply of urea, however, the number of strains that consumed 0.5 g or more ammonium increased to 32 and 35 strains, respectively, or at very high rates as compared with the pre-administration figure. As noted above, the test bacteria were largely those belonging to specific strains, such as L. acidophilus and L. plantarum.

A generally similar tendency was observed with ammonium chloride.

TABLE 5

| | Numbers of strains of lactic acid bacteria classified by ammonium consumption | | | | | |
|---|---|---|---|---|---|---|
| | Ammonium sulfate conspn* | | | Ammonium chloride conspn* | | |
| | Under 0.1g | 0.1 –0.5g | Over 0.5g | Under 0.1g | 0.1 –0.5g | Over 0.5g |
| Before urea admn (62) | 53(86) | 8(12) | 1( 2) | 57(92) | 5( 8) | 0 |
| During urea admn (70) | 8(10) | 30(44) | 32(46) | 15(21) | 38(54) | 17(25) |
| After urea admn (67) | 4( 6) | 35(52) | 28(42) | 10(15) | 42(62) | 15(23) |

*Ammonium consumption in medium containing 1 g ammonium salt per 10 ml of the medium.
The numerical values in the parentheses represent percentages on the bases of total numbers (given at the left ends) of the strains tested.

Generally the same tendency was seen with the cellulose-decomposing bacteria, as shown in Table 6. The table indicates that the supply of ammonium salts or urea caused the growth and multiplication of only the strains having strong ammonium-utilizing abilities and that mass mutation took place in the rumens of the test animals.

TABLE 6

Numbers of strains of cellulose-decomposing bacteria classified by ammonium consumption

| | Ammonium sulfate conspn** | | | Ammonium chloride conspn** | | |
|---|---|---|---|---|---|---|
| | Under 0.1g | 0.1 –0.5g | Over 0.5g | Under 0.1g | 0.1 –0.5g | Over 0.5g |
| Before urea admn (53) | 40(75) | 13(25) | 0 | 37(70) | 10(19) | 6(11) |
| During urea admn (46) | 6(14) | 29(62) | 11(24) | 0 | 20(44) | 26(56) |
| After urea admn (53) | 5( 9) | 32(60) | 16(31) | 0 | 25(47) | 28(28) |

**Ammonium consumption in medium containing 1 g ammonium salt per 10 ml of the medium. The numerical values in the parentheses represent percentages on the bases of total numbers (given at the left ends) of the strains tested.

EXAMPLE 3

In this example, the method of obtaining bacteria with the plate media as described in the preceding examples and the method of obtaining bacteria with the ruminant stomach were alternately employed to choose strains with exceeding ammonium-utilizing abilities out of the test bacteria.

By way of examplification, a test strain (lactic acid bacteria = *L. plantarum*, U-48) was inoculated on a lactobacillus selective medium containing 2.5% ammonium salt. In the same manner as described in Example 1 the ammonium salt concentration was gradually increased to about 8–10 percent. Then, the bacteria were collected from the plate and dried to powder in the usual way. The dry bacterial powder thus obtained was weighed (4.8 × $10^7$/kg/day) and fed to goats, along with a urea-containing feed (20 g/kg/day), for one week. The urea concentration was gradually raised up to 9 percent.

From the rumens of the goats fed in this manner the bacteria given together with the feed were detected. Thenceforth the plate culture method and the method of using the ruminant stomach were alternately employed to obtain a strain having a great ammonium-utilizing ability from the test bacteria.

EXAMPLE 4

In the procedure of Example 2 for acquiring an improved strain from the stomachs of ruminants, the ammonium salt concentration was gradually increased from week to week.

As an alternative, a strain with a good ammonium-utilizing ability can be selectively obtained from the rumens by giving large doses of urea within short periods of time, although it involves some danger to the animals. This example pertains to the alternative procedure.

Figure 2:
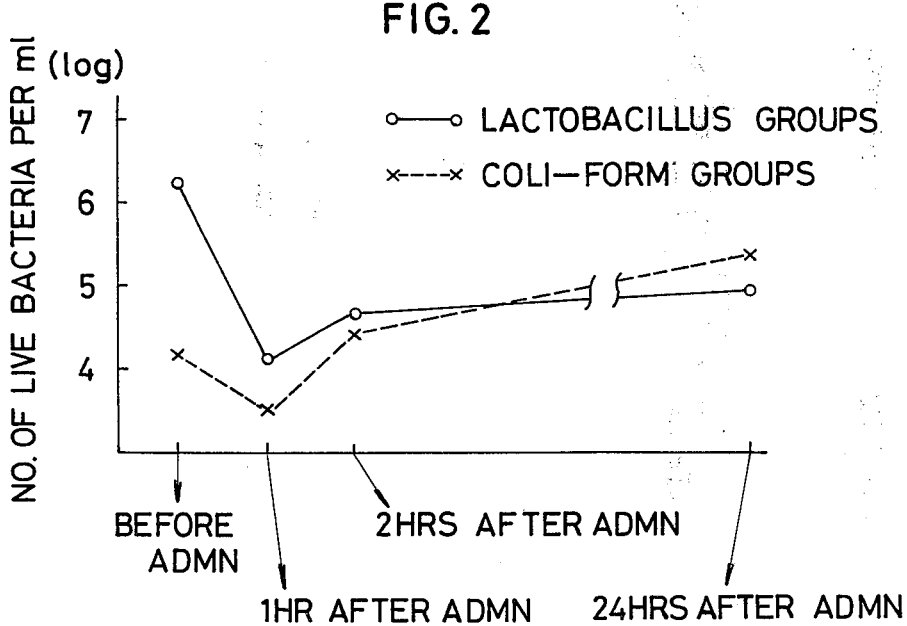
FIG. 2 is a graph showing changes in the viable counts of the rumenal bacteria with acute administration of urea.

In one experiment, a test strain (lactic acid bacteria = *L. plantarum*, U-48) was given to a test goat at a rate of 4.3 × $10^7$/kg/day for one week, and then urea was administered at a rate of 1.0 g/kg. The goat suffered from acute ammonia poisoning and repeated tonic convulsions. It was medically treated but was seriously emaciated the next day. Later it recovered the health. During the experiment period the bacterial flora in the rumen underwent changes as shown in FIG. 2.

Similarly a test goat was caused to take the same test strain (lactic acid bacteria = *L. plantarum*, U-48) at a smaller rate of 3.8 × $10^7$/kg/day for one week and then was given a single dose of urea at a rate of 0.5 g/kg. The goat was attacked by ammonia poisoning, too, but the condition was not as deadly as in the aforesaid experiment.

Five days later when the goat completely recovered its physical strength, it was given one gram of urea per kilogram of its body weight. This caused light symptoms of ammonia poisoning including spasms in the muzzle wing for a short period of time. The conditions of bacterial flora in the rumen were as represented in FIG. 3.

The strain with its ammonium salt-utilizing ability improved in this way was inoculated on the culture medium of Example 1 which contained a high concentration of an ammonium salt. The bacteria were separated and collected, given to a ruminant, e.g., goat, again in the same manner as above described, and then urea was given at a rate of 1 g/kg to improve the ammonium salt-utilizing ability of the bacteria. The foregoing procedure was repeated until a strain was obtained which could grow on a plate medium for LBS lactic acid bacteria containing 10% ammonium salt.

It is thus clear that a large temporal dose of urea is useful in improving the ammonium salt-utilizing ability of lactic acid bacteria, although it accompanies some physical danger.

In order to examine the changes in viable count of the bacteria in the rumen with an acute dose of urea, a test goat was continuously rationed with a feed containing the lactic acid bacteria with an improved ammonia-utilizing ability for one week and then was administered with an acute dose of urea in an amount of 1 g/kg. The results were as given in Table 7. FIG. 2 is a graphic representation of the same data.

Table 7

| Counting point of time | Before administration | 1 hr after admn | 2 hrs after admn | 24 hrs after admn |
|---|---|---|---|---|
| Lactobacillus groups | 4.2×$10^6$ | 1.9×$10^4$ | 6.0×$10^4$ | 1.0×$10^5$ |
| Coli-form groups | 2.2×$10^4$ | 5.6×$10^3$ | 5.9×$10^4$ | 2.8×$10^5$ |

(Numbers of live bacteria/ml)

Also, the changes in viable count of the bacteria in the rumen with a subacute dose of urea were examined by supplying a test goat with lactic acid bacteria having an improved ammonia-utilizing ability and urea at a rate of 0.5 g/kg, and then giving four days later an acute dose of 1.0 g/kg of urea. The results were as shown in Table 8 and as charted in FIG. 3.

Table 8

| Counting point of time | Before administration | 15 min after admn | 1 hr after admn | 2 hrs after admn | 24 hrs after admn |
|---|---|---|---|---|---|
| Lactobacillus groups | $4.0 \times 10^4$ | $1.5 \times 10^4$ | $1.2 \times 10^4$ | $3.4 \times 10^4$ | $1.2 \times 10^4$ |
| Coli-form groups | $1.5 \times 10^6$ | $6.6 \times 10^5$ | $2.5 \times 10^4$ | $2.0 \times 10^4$ | $6.0 \times 10^4$ |

(Numbers of live bacteria/mil)

EXAMPLE 5

Goats were used as test ruminants and the following experiment was conducted. Fifteen 2-year-old goats of Saanen breed were divided into three groups, i.e., control, test, and standard groups. The control group was fed on a feed containing 3% urea. The test group was fed on a 3%-urea feed containing a bacterial preparation manufactured by the method of the invention at a rate of $4.5 \times 10^7$/kg/day. The standard group was given a commercially available urea-free feed. All were fed for 100 days.

After the test period, the average body weights of the goats of the standard and test groups exceeded that of the control group by 11.1 and 12.3 percent, respectively.

In the early period of rationing with the urea-containing feed, some of the control goats indicated lack of appetite and vigor, whereas the goats of the test group had as hearty an appetite as those of the standard group.

We claim:

1. In a process for conditioning a rumen flora containing a relatively high number of lactobacillus groups and a relatively small number of coliform groups to improve the ammonium salt utilizing ability thereof by serial passage and culturing of microorganisms on a streak inoculated plate culture medium containing the maximum ammonium salt concentration compatible with serial passage culture growth, the improvement which comprises:
   a. further culturing colonies of said microorganisms which have been cultured in said streak inoculated plate culture medium containing the maximum ammonium salt concentration compatible with serial passage culture growth by repeatedly streaking said colonies over the surface of said culture medium until the entire surface thereof is covered with colonies and said culture medium is enriched with sufficient metabolic products from the growth of said microorganisms therein to condition said microorganisms to grow in the presence of ammonium salt concentrations higher than said maximum; and
   b. transferring colonies of the resultant conditioned microorganisms to a new culture medium having an ammonium salt concentration higher than said maximum, and repeating step a) in said new culture medium.

2. A process according to claim 1 wherein said microorganism is selected from the group consisting of lactobacillus, clostridium, cellulose-decomposing bacteria, subtilis and yeast.

3. A process according to claim 2 wherein said microorganism is a lactobacillus selected from the group consisting of *Lactobacillus plantarum, lactobacillus fermenti, Lactobacillus acidophilus, Lactobacillus brevis, Streptococcus faecalis, Streptococcus lactis* and *Clostridium butyricum*.

4. A process according to claim 3 wherein said rumen flora is dominant in *Lactobacillus acidophilus, Lactobacillus plantarum, Streptococcus lactis* or *Streptococcus faecalis*.

5. A process according to claim 2 wherein said maximum ammonium salt concentration is about 7.5 percent.

6. A process according to claim 2 further comprising transferring the resultant conditioned microorganism into the rumen of a living ruminant to enhance the conversion of ammonia therein into somatic proteins.

7. A process according to claim 6 wherein said conditioned microorganism is separated, collected and pulverized or granulated with an excipient prior to said transfer.

8. A process according to claim 7 wherein said transferred conditioned microorganism comprises a combination of *Lactobacillus plantarum, Clostridium butyricum* and *Streptococcus faecalis*.

* * * * *